United States Patent [19]
Cush et al.

[11] Patent Number: 5,210,404
[45] Date of Patent: May 11, 1993

[54] OPTICAL SENSOR INCLUDING A BRAGG GRATING STRUCTURE FOR ENHANCED SENSITIVITY

[75] Inventors: Rosemary Cush, Northampton; William J. Stewart, Blakesley, both of England

[73] Assignee: Gec-Marconi Limited, England

[21] Appl. No.: 885,481

[22] Filed: May 19, 1992

[30] Foreign Application Priority Data

Jun. 7, 1991 [GB] United Kingdom ............... 9112262

[51] Int. Cl.$^5$ ................................................ H01J 3/14
[52] U.S. Cl. .................................. 250/216; 356/128; 359/572; 385/37
[58] Field of Search ............... 250/216, 226; 359/130, 359/572; 385/36, 37, 141; 356/128, 432

[56] References Cited

U.S. PATENT DOCUMENTS

| | | | |
|---|---|---|---|
| 4,815,843 | 3/1989 | Tiefenthaler et al. | 356/128 |
| 4,857,273 | 8/1989 | Stewart | 422/68 |
| 5,082,629 | 1/1992 | Burgess, Jr. et al. | 422/82.11 |

OTHER PUBLICATIONS

C. Dahne, et al, "Detection of Antibody–Antigen reactions at a glass liquid interface: A novel fibre–optic concept", Proc. SPIE, vol. 514 (1984), p. 75.
P. B. Daniels, et al, "Surface plasmon resonance applied to immunosensing", Sensors and Actuators, 15 pp. 11-18, (Feb. 8, 1988).
B. Liedberg, et al., "Surface plasmon resonance for gas detection and biosensing", 4, pp. 299-304 (May–Jun. 1983).
P. M. Nellen, et al, "Integrated optical input grating couplers as biochemical sensors", Sensors and Actuators, 15 (Mar. 1988) pp. 285-295.
E. E. Hardy, et al, "Coated optical guides for spectrophotometry of chemical reactions", Nature, vol. 257, Oct. 1975, pp. 666-667.
M. T. Flanagan, et al, "Surface plasmon resonance and immunosensors", Electron. Letts., Nov. 8, 1984, vol. 20, No. 23, pp. 968-970.
N. J. Harrick, "Internal Reflection Spectroscopy", 1967, John Wiley & Sons.

Primary Examiner—David C. Nelms
Assistant Examiner—T. Davenport
Attorney, Agent, or Firm—Kirschstein, Ottinger, Israel & Schiffmiller

[57] ABSTRACT

This invention describes a technique for improving the sensitivity of a resonant mirror sensor which has particular applications in areas involving sensing at an interface such as immunosensing using immobilized antibodies. By the introduction of a Bragg grating structure in the sensor, there is produced enhanced dispersion and hence enhanced sensitivity in the region close to the band edge. This improves the detection limit of the sensor without changing the composition or involving the sensor size and allows more sensitive operation at reduced incident angles.

4 Claims, 3 Drawing Sheets

OPTICAL SENSOR INCLUDING A BRAGG GRATING STRUCTURE FOR ENHANCED SENSITIVITY

This invention relates to an optical sensor including a Bragg grating structure which improves the sensor's sensitivity by means of enhanced dispersion occuring close to the stop band of the grating.

Optical techniques have been utilized for some time in the field of sensors, monitoring reactions by measuring changes in absorption, fluoresence, scatter and refractive index often remotely by the use of optical fibres. In particular, for applications such as immunosensing, great interest has been shown in evanescent optical sensors. In these devices, a layer which undergoes an optical change on sensing is immobilized onto the surface of a device so that the evanescent field of the light penetrates the sensing layer. The layer may be, for example, a chemical substance which changes colour on exposure to physical changes, such as heat, or to chemical changes on exposure to a particular molecule. For a biological sensor, monoclonal antibodies may be used as the sensing layer, which bind highly specifically to defined antigens, so changing the sensing layer composition. Suitable devices include prisms, waveguides, gratings and fibres. Any reactions occurring at the sensing layer affects the evanescent field and hence the optical properties of the device. Using the evanescent wave as the sensing element has a number of advantages:

a) the light path is separated from the sensing region;
b) the light probes only a surface layer, not seeing the bulk of the sample;
c) the test volume is only that which the evanescent field occupies—a few nanoliters.

In this way, the bulk of the sample does not interfere with the light either on its path to and from the sensing region or at the sensing layer, so removing the requirements to separate out, for example, the cells in a blood sample. The small volume means that pin-prick samples may be used, so reducing the discomfort caused to the patient, particularly where repeated measurements are to be made.

Both absorbing and fluorescing total internal reflection (TIR) sensors have been used for some time. In this technique, light is reflected off a glass-air boundary, the reflected light being monitored to detect absorption by, or fluorescence of, molecules at the device surface. For this to be successful, either the wavelength used must correspond to the natural absorption or fluorescence bands of the molecules, or the molecule must be labelled. This greatly restricts the range of molecules which may be detected using this technique or increases the complexity of the test, both of which are undesirable.

A number of techniques have been used to increase the sensitivity of TIR spectroscopy and fluorimetry. All involve increasing the number of reflections at the interface where the sensing layer is bound. Harrick, ("Internal Reflection Spectroscopy", John Wiley and Sons Ltd., (1967)) uses multiple reflections at the prism surface. Other techniques involve the use of light pipes (E. E. Hardy et al, "Coated Optical Guides for Spectrophotometry of Chemical Reactions", Nature, Vol. 257, Oct. 23 (1976) 666) and waveguides (C. Dahne et al, "Detection of Antibody-Antigen Reactions at a Glass Liquid Interface: A Novel Fibre-Optic Sensor Concept", Proc. SPIE Vol. 514 (1984) p75). These techniques allow very sensitive assays to be made but all involve some kind of labelled reagent so increasing the complexity of the test.

More recently attempts have been made to sense reactions by measuring the effect on the phase of light passing through the sensing layers, a consequence of changes in the thickness and refractive index. These include surface plasmon resonance sensors, resonant mirror (GB-A-2,174,802B, U.S. Pat. No. 4,857,273) and resonant grating (GB-A-8900566.5), WO(GB)89/01461) sensors and waveguide sensors. These techniques allow a direct measurement of the binding reaction without the need for labels, and so are applicable to a wide range of sensing applications.

The resonant mirror biosensor described in GB-A-2,174,802B and U.S. Pat. No. 4,857,273 is an evanescent wave sensor, based on total internal reflection, where a resonant cavity is used to enhance the light intensity at the device surface, hence increasing the sensitivity. When light is totally internally reflected from a boundary, it undergoes a phase change. The size of the phase change depends upon the refractive indices of the bounding materials, the wavelength of the light and the angle of incidence. Any changes at the boundary, such as antibody-antigen binding reactions, will alter the phase change. However, for a simple high/low index boundary, the phase change is very slight and so the device is not very sensitive. In order to increase sensitivity, the resonant mirror device incorporates a resonant structure at the boundary, consisting of a high-low index pair of dielectric layers. The layer pair acts rather like a Fabry-Perot cavity. One "mirror" of the cavity consists of the low index layer bounded by the two high index materials. Some of the light is reflected from the lower boundary "tunnels", via the evanescent field, into the high index layer, a process known as frustrated total internal reflection. This layer therefore acts as a partially transmitting mirror, the degree of transmission being determined by the low index (or coupling) layer thickness. The second "mirror" of the cavity is the upper high index/low index boundary where total internal reflection occurs. This boundary is therefore 100% reflecting.

As with a Fabry-Perot cavity, resonance only occurs when the round trip phase delay between the mirrors is equal to $2\pi$ radians. At resonance, the intensity of light in the cavity is high, at other times it is virtually zero. As the cavity has one totally reflecting boundary, all light is reflected from the resonant mirror device, both on and off resonance. However, the phase of the reflected light undergoes an additional change of $\pi$ radians on resonance. It is the phase of the reflected light which is monitored in the resonant mirror device.

The incident angle at which resonance occurs is such that the total round trip phase delay, which consists of the distance travelled between the two boundaries of the high index layer together with the phase change on reflection at each boundary, is equivalent to a whole number of wavelengths. Any binding reaction occurring at the top surface alters the phase change on reflection at the upper boundary. To achieve resonance the incident angle must be adjusted to compensate for this. In a low loss system, the range of angles over which the resonant phase change occurs is very narrow and so very small changes in the resonant angle corresponding to small surface changes, can be detected.

So by increasing the number of times the light is reflected from the upper boundary the sensitivity of the device is increased significantly. The sensitivity is limited in practice only by the number of reflections that may occur in the device—even very small light loss, due to scatter or absorption, become significant after many reflections. In addition, the device must be of finite length. The resonant width is typically a few minutes of arc, corresponding to a propagation length of ~3 mm.

Light with its electric vector perpendicular to the plane of incidence (TE) undergoes a phase change on reflection which is different to that for light in the orthogonal polarization (TM), so the angle at which resonance occurs differs for the two polarizations. The extra information available from measuring angle shifts for both polarization components is a very valuable feature of the resonant mirror, allowing values for the average thickness and refractive index of the sensing layer to be calculated.

For practical device light must be coupled into the high index substrate. One way to do this is by using a prism shaped substrate, however a variety of alternative techniques may be used such as a grating, fresnel lens or various lens/prism combinations.

According to the invention there is provided an optical sensor comprising a dielectric resonant cavity including a dielectric resonant layer bounded at its opposite plane faces by a sensing layer and a coupling layer, a substrate layer supporting said coupling layer and a Bragg grating provided in any one of said layers to enhance the sensitivity of the optical sensor, the period of the grating, $\Delta$, being selected so that a forbidden band is formed for a range of wavevectors, centred on the wavevector, K, which satisfies the condition $K.\Delta = m\pi$ (m is an integer), such that the resonant wavevector of the sensor is outside the forbidden band, in a range adjacent the edge of the forbidden band, the size of the forbidden band being dependent upon amplitude of the grating variation.

In the region close to the band edge, the Bragg grating provides at least 10% increase in the sensitivity of the optical sensor.

The grating structure improves this detection limit of the sensor without changing the composition or increasing the sensor size and allows more sensitive operation at reduced incident angle.

The invention will now be described further by way of example with reference to the accompanying drawings in which.

Figure 1:
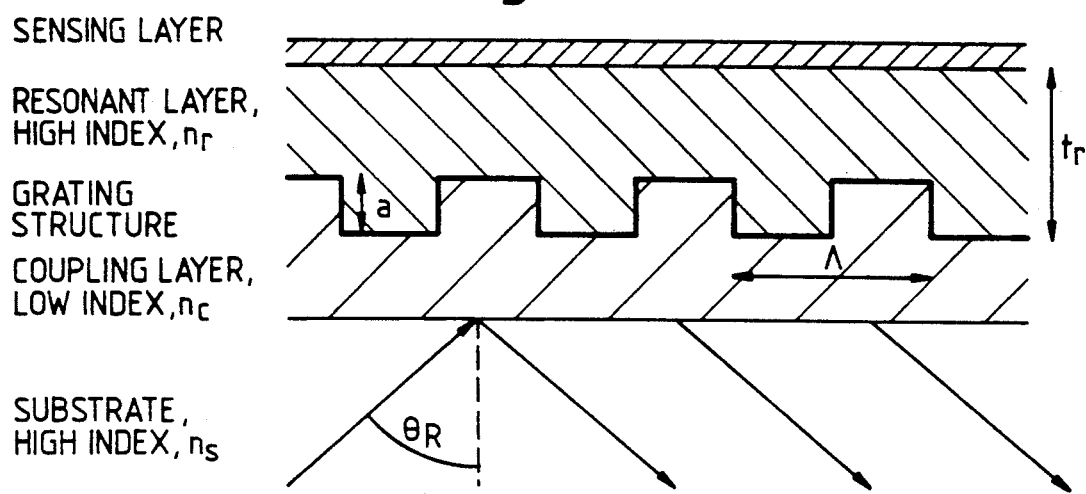
FIG. 1 illustrates a Bragg grating enhanced resonant mirror sensor embodying the present invention.

Referring to FIG. 1, there is illustrated a resonance mirror sensor embodying the invention, which includes a resonant cavity having a resonant layer 11 of thickness $t_r$ and high refractive index $n_r$ bounded at its opposite plane faces by a sensing layer 12 and a coupling layer 13 of low refractive index $n_c$. The coupling layer 13 is supported on a substrate 14 of high refractive index $n_s$. A Bragg grating structure 15 of amplitude a and a grating period $\Delta$ is provided in the resonant layer 11 to enhance the sensitivity of the resonant mirror sensor.

SENSITIVITY

Figure 2:
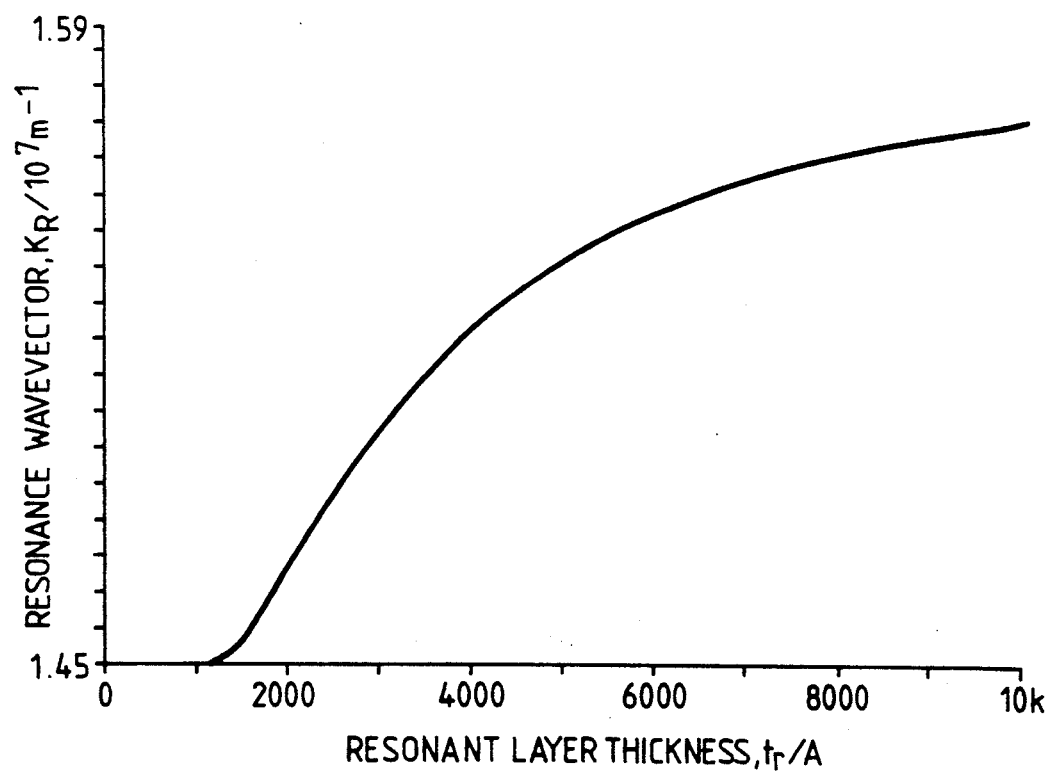
FIG. 2 is a graph showing variation in resonance wavevector with resonant layer thickness for a device without Bragg grating enhancement, the slope of the curve indicating the sensitivity.

The sensitivity of the device to changes in the sensing layer is proportional to (for thin sensing layers) $\delta K_R/\delta t_r$, (where $K_R = k_O n \sin\theta_R$, $\theta_R$ is the angle of resonance, $k_O$ is the vacuum wavevector, n is the substrate refractive index and $t_r$ is the thickness of the resonant layer). This is determined by the dispersion relation for the structure, as shown in FIG. 2 for a device without enhancement. The maximum slope of this curve, and hence the maximum sensitivity, is determined by the refractive indices and thicknesses of the particular device structure. Due to fabrication difficulties, it is not usually possible to use resonant layers with refractive indices >2.3, thereby limiting the sensitivity. The use of a Bragg grating allows us to increase this slope without changing the device composition.

The propagation of radiation in periodic medium gives rise to many common physical phenomena, including X-ray diffraction in crystals and the band structures of metals, and is utilized in many optical devices, for example, diffraction gratings, holograms, DFB lasers, DBR lasers, high reflectivity Bragg mirrors, acousto-optic filters and Solc filters. A common feature is that when the wavevector of the radiation, K, satisfies the condition $K.\Delta = m\pi (\alpha$ is the period of the variation, $\Delta$ is the corresponding vector, m is an integer), a 'forbidden band' occurs. Under these conditions radiation is reflected back along the propagation directions, so preventing forward transmission. This effective attenuation gives rise to a complex propagation constant within the band. The size of the bandgap depends on the strength of the periodic variation.

Figure 3A:
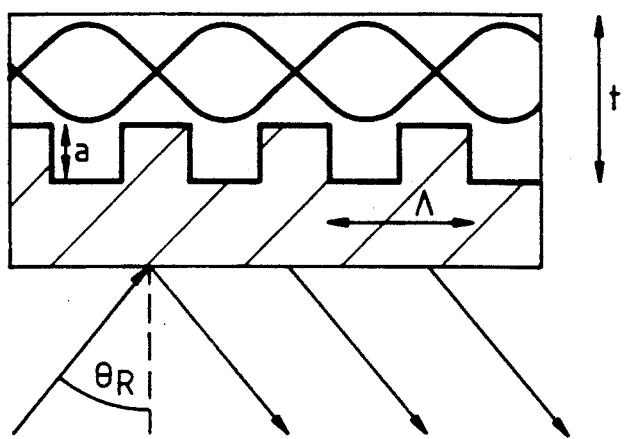
FIG. 3a shows a Bragg grating structure with the standing wave maxima occuring where the resonant layer is thicker.
Figure 3B:
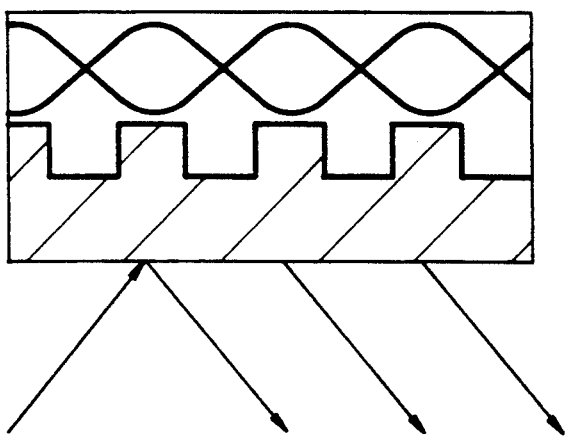
FIG. 3b shows a Bragg grating structure with the standing wave maxima occuring where the resonant layer is thinner.
Figure 4:
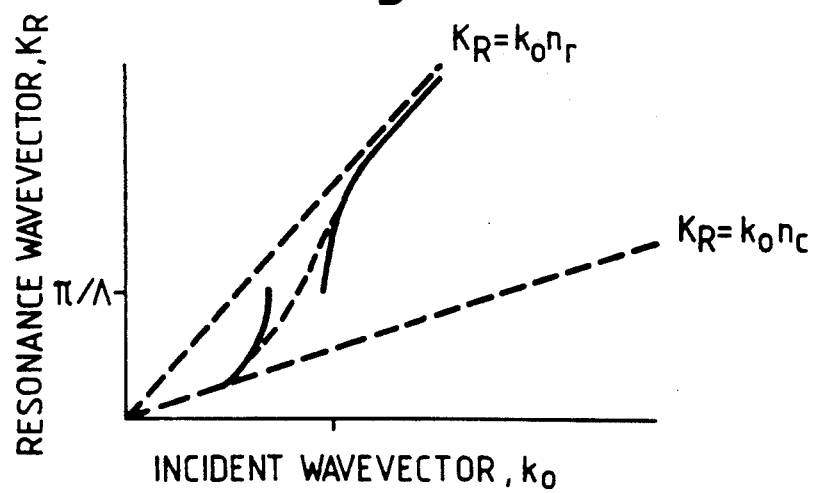
FIG. 4 is a graph showing Bragg modified dispersion relation (Wrt.$k_O$) of resonance wavevector $K_R$ and incident $k_O$.
Figure 5:
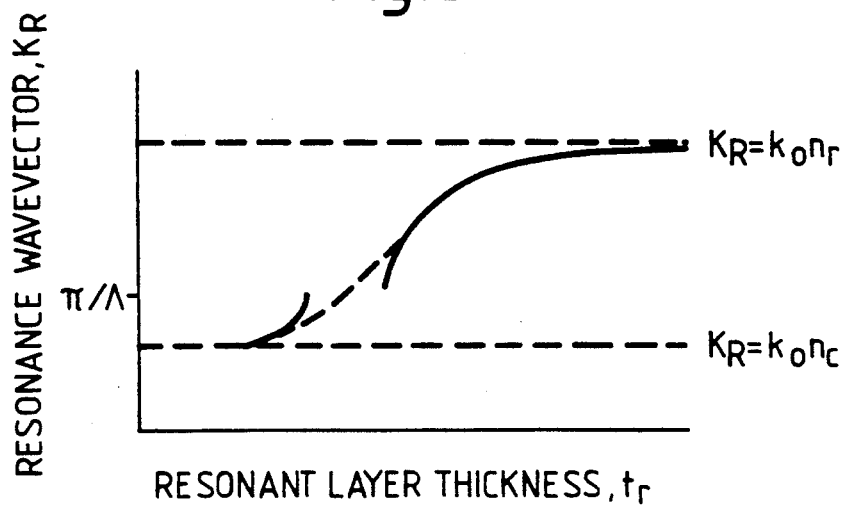
FIG. 5 is a graph showing Bragg modified dispersion relation (Wrt $t_r$) of resonance wavevector $K_R$ and resonance layer thickness $t_r$.

Effect of Bragg grating on resonant mirror device sensitivity: Close to the edge of the bandgap, the periodicity has an effect on the wavevector, K, leading to an enhanced dispersion. Effectively, for values of $k_O$ close to the bandgap, the corresponding values of K are slightly less or slightly more than for the unperturbed system. This can be envisaged as arising from the standing waves which occur when multiple forward and backward reflections take place in the periodic structure. For an example we will consider the component of light, $K_R = k_O n \sin \theta_R$, propagating through a resonant mirror device with a periodically varying resonant layer thickness, $t_r(x) = t_{rO} + \Delta t_r \cos(2\pi x/\Lambda)$. Away from the bandgap the radiation propagates through the structure and will 'see' an average value of resonant layer thickness of $t_{rO}$. However, when standing waves form, the field distribution is quite different. As the system is symmetrical, the standing waves must form in either of two positions, as shown in FIG. 3. In position a), the standing wave maxima occur where the resonant layer is thicker, therefore the light 'sees' a device with a thicker resonant layer, with a correspondingly higher value of $K_R$ for a given $k_O$. In position b), the light maxima occur where the resonant layer is thinner, giving rise to a lower value of $K_R$ for a given $k_O$. This distortion of the dispersion relation leads to enhanced sensitivity of $K_R$ to changes in $k_O$ (and similarly to changes in $t_r$, or the sensing layer) close to the band edges. This can be seen in FIGS. 4 and 5 which show the dispersion relations for a resonant mirror device for $K_R$ against $k_O$ and $t_r$ (with fixed $t_r$ and $k_O$ respectively). These curves show only the real part of $K_R$. As there is always some coupling of light in and out of the resonant layer, there will always be an imaginary component, but for weak coupling the effect should be negligible.

The periodic variation may be formed in a number of ways, for example, a) Refractive index variations: The refractive index of the resonant layer, coupling layer or the substrate may be made to vary periodically, for example, by ion indiffusion into glass or photobleaching/photopolymerization in polymers.

b) Thickness variation: The thickness of any of the constituent layers may be made to vary periodically, for example, by etching or embossing a grating structure into the layers.

c) Surface layer: A surface layer of periodically varying index or thickness may be formed on the device. This layer may even form the sensing layer. In this case, reaction would then change the bandgap, resulting in a change in dispersion and a shift in $\theta_R$.

By changing the period of the variation, the bandgap may be moved to suit any value of $K_R$. This is an advantage as it allows an enhancement of dispersion for values of $K_R$, and hence $\theta_R$, below that for optimum sensitivity in the unperturbed device, so allowing operation at incident angles closer to the normal and/or using lower refractive index substrates. These are important considerations for the practical implementation of the sensor.

The range over which enhanced absorption occurs is narrow, and as the increase in sensing layer thickness moves $K_R$ away from the band edge, the sensitivity will decrease. This will be of advantage in systems required to operate over a large dynamic range, resulting in a sensor device which is more sensitive to small analyte quantities than to larger ones, giving similar resonant angle shifts for a given percentage change in analyte concentration throughout the desired sensing range.

To achieve this effect, the zero position of the device should be set on the upper edge of the bandgap. On the lower edge, the grating will also cause light to couple out of the structure with a detrimental effect on system sensitivity. As the starting conditions are likely to vary, due to the variations in the refractive index of the test solution, it will be preferable to use this device with a tunable source, so that $k_o$ may be varied at the beginning of the test.

EXAMPLE OF RESONANT MIRROR SENSOR

The following structure is given as an example of a possible device structure and composition:
Wavelength of operation: 633 mm
Substrate F2 glass: refractive index 1.62
Coupling layer: silica (e-beam evaporated), refractive index 1.46, thickness 8000 Å
Resonant layer: alumina (e-beam evaporated), refractive index 1.6, average thickness, 1930 Å
To operate at $\theta_R = 66°$
Unenhanced device sensitivity, $$\frac{\delta K_R}{\delta t_r} = 8.1 \times 10^{13} \, m^{-2}$$

The effect of the Bragg grating can be modelled exactly (ref: A. Yariv and P. Yeh, "Optical Waves in Crystals", John Wiley and Sons, Chapter 6, p155) or approximated by coupled mode theory (ref: K. Sakuda and A. Yariv, "Analysis of Optical Propagation in Corrugated Dielectric Waveguide", Opt. Commun. 8 (1973) p1). In the limit of weak coupling into the resonant structure (thick coupling layer), the resonant mirror device may be treated as a three layer dielectric structure and the resonance conditions obtained by solving the wave equation for these boundary conditions, as with a three layer waveguide structure. This is plotted in FIG. 6. For a device with a Bragg grating, using coupled mode theory we may derive the coupling coefficient, (TE resonance, ref: K. Sakuda and A. Yariv, "Analysis of Optical Propagation in Corrugated Dielectric Waveguide", Opt. Commun. 8 (1973) p1), $$= \frac{\pi k(n_r^2 - n_c^2)}{3 n_r} \cdot \left(\frac{a^3}{t}\right) \cdot \left[\frac{3(\lambda_0/a)}{2\pi(n_r^2 - n_c^2)^{\frac{1}{2}}} \quad \frac{3(\lambda_0/a)^2}{4\pi^2(n_r^2 - n_c^2)}\right]$$

where the terms are defined in FIG. 1.

For this example we will choose a periodic variation with an amplitude of 100 Å and period 214 nm, giving $k = 2.88 \times 10^5 \, m^{-1}$. The bandgap, which occurs when $K_R = \pi/\Lambda$, will therefore be centered around $t_r = 1891$ Å and the size of the bandgap, is 74 Å.

The dispersion close to the upper band edge, where $k_O = k_{Ou}$, is given by, $$K'_R = \pi/\Lambda + (\pi/\Lambda - K_R)^2 - k^2$$

(where $K_R$ is the unperturbed value, $K'_R$ the value with the grating).

By differentiation we may derive an expression for the enhanced sensitivity of the device and calculate that, $$\frac{\delta K'_R}{\delta t_r} = 2.68 \times \frac{\delta K_R}{\delta t_r}$$

Figure 6:
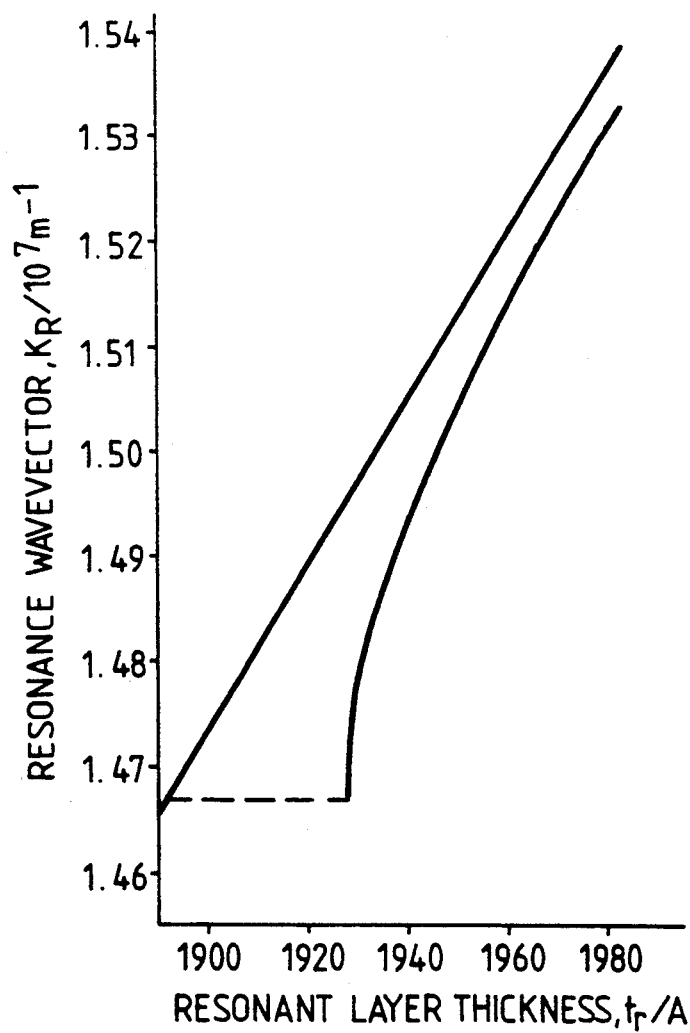
FIG. 6 is a graph showing normal and enhanced dispersion in the region of the bandgap.

By decreasing the grating period, hence moving the band edge closer to the resonance point, even greater enhancement is possible. The normal and enhanced dispersion curves in the region of the bandgap for this device are shown in FIG. 6.

By introduction of the Bragg grating structure into a resonant mirror device there is produced enhanced dispersion and hence enhanced sensitivity of the device in the region close to the band edge. This improves the detection limit of the device without changing the composition or increasing the device size and allows more sensitive operation at reduced incident angles.

We claim:

1. An optical sensor comprising a dielectric resonant cavity including a dielectric resonant layer bounded at its opposite plane faces by a sensing layer and a coupling layer; a substrate layer supporting said coupling layer and a Bragg grating provided in any one of said layers to enhance the sensitivity of the optical sensor, the period of the grating, $\Lambda$, being selected so that a forbidden band is formed for a range of wavevectors, centered on the wavevector, K, which satisfies the condition $K.\Delta = m\pi$ (m is an integer), such that the resonant wavevector of the sensor is outside the forbidden band, in a range adjacent the edge of the forbidden band, the size of the forbidden band being dependent upon amplitude of the grating variation.

2. An optical sensor as claimed in claim 1, in which the grating period is such that the sensitivity of the sensor is enhanced by at least 10%.

3. An optical sensor as claimed in claims 1, in which the Bragg grating is provided in any one of said layers by periodically varying the thickness thereof.

4. An optical sensor as claimed in claims 1, in which the Bragg grating is provided in any one of said layers by periodically varying the refractive index thereof.

* * * * *